(12) United States Patent
Khatri et al.

(10) Patent No.: US 7,868,123 B2
(45) Date of Patent: Jan. 11, 2011

(54) DERIVATIZED TERTIARY AMINES AND USES THEREOF

(75) Inventors: Chetan A. Khatri, Belle Mead, NJ (US); Binoy K. Bordoloi, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 573 days.

(21) Appl. No.: 11/942,035

(22) Filed: Nov. 19, 2007

(65) Prior Publication Data
US 2009/0131938 A1 May 21, 2009

(51) Int. Cl.
*C08G 18/71* (2006.01)
(52) U.S. Cl. .............................. 528/68; 528/69; 528/310
(58) Field of Classification Search ................... 528/68, 528/69, 310
See application file for complete search history.

(56) References Cited

U.S. PATENT DOCUMENTS

| | | | |
|---|---|---|---|
| 2,874,138 A | | 2/1959 | Jackson |
| 3,946,014 A | | 3/1976 | Fuger et al. |
| 4,458,029 A | * | 7/1984 | Munk .......................... 502/171 |
| 4,471,103 A | * | 9/1984 | Miyake et al. ................ 528/65 |
| 5,091,497 A | * | 2/1992 | Grogler et al. ................ 528/76 |
| 6,491,845 B1 | * | 12/2002 | Schile .................... 252/182.24 |
| 7,576,167 B2 | * | 8/2009 | Mori et al. ..................... 528/13 |
| 2004/0219214 A1 | | 11/2004 | Gravett et al. |
| 2007/0276121 A1 | | 11/2007 | Westergom |
| 2008/0213597 A1 | * | 9/2008 | Li ................................ 428/414 |

FOREIGN PATENT DOCUMENTS

EP  1698325 A  6/2006

OTHER PUBLICATIONS

International Search Report re: PCT/US2008/083996 dated May 27, 2009.

* cited by examiner

*Primary Examiner*—Bernard Lipman

(57) ABSTRACT

The invention relates to a tertiary amine intermediate represented by the following formula, and electrophilic monomers derived therefrom. The invention also relates to adhesives or sealants derived from such electrophilic moieties.

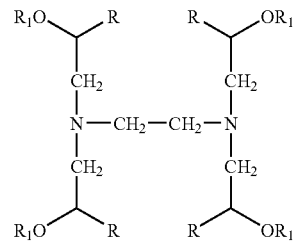

where $R=CH_3$, H, $CH_3CH_2$ or other alkyl group; and $R_1=H$, $C(O)CH_2OCH_2COOH$, $C(O)(CH_2)_nCOOH$ with $n=1$-4, or combinations thereof.

13 Claims, No Drawings

DERIVATIZED TERTIARY AMINES AND USES THEREOF

FIELD OF THE INVENTION

The invention relates to derivatized tertiary amines; an adhesive or sealant comprising (1) one or more electrophilic moiety or derivatized tertiary amine monomer and (2) one or more nucleophilic entity; and an adhesive or sealant comprising the reaction product of (1) and (2).

BACKGROUND OF THE INVENTION

When surgery is performed, there is an unmet need for an adhesive or sealant material that may be used internally to seal the wound site and prevent fluid leakage in, for example, a vessel anastomosis or lung resection, or hemostasis in a partial nephrectomy repair.

More specifically, it is desirable to have an adhesive or sealant comprised of components that can polymerize when needed to form an adhesive or sealant polymer in situ. If a liquid adhesive or sealant is desirable, the components of such an adhesive or sealant should be water soluble or at least soluble in a water-miscible solvent, and should be reasonably stable in water or water-miscible solvent at least at the time of application. Additionally, the adhesive or sealant polymer that is formed in situ should adhere to tissue and biodegrade over time into degradation products that are water soluble, so that the degradation products can be eliminated naturally either by secretion or incorporation into the natural biochemical cycle. For internal medical applications, each of the components that make up the adhesive or sealant, the resultant polymer and the degradation products thereof should be biocompatible.

If the adhesive or sealant components are to be used in powder or solid form, i.e., with or without a substrate, the components of the adhesive or sealant should be water soluble, so that upon contact with physiological fluid at the site of application, the adhesive or sealant components can solubilize and react with each other and collagen at the site of application. Nevertheless, the adhesive or sealant polymer that is formed in situ should still adhere to tissue and biodegrade over time into degradation products that are water soluble. Additionally, for internal medical applications, each of the components that make up the adhesive or sealant, the substrate if used, the resultant polymer and the degradation products thereof should be biocompatible.

SUMMARY OF THE INVENTION

The invention relates to derivatized tertiary amines; an adhesive or sealant comprising (1) one or more electrophilic moiety or derivatized tertiary amine monomer and (2) one or more nucleophilic entity; and an adhesive or sealant comprising the reaction product of (1) and (2).

DETAILED DESCRIPTION OF THE INVENTION

The invention relates to derivatized tertiary amines; an adhesive or sealant system comprising (1) one or more electrophilic moiety or derivatized tertiary amine monomer and (2) one or more nucleophilic entity having amine functionality; and an adhesive or sealant comprising the reaction product of (1) and (2).

The adhesive or sealant according to the present invention has multiple medical applications and may be used in many types of surgery, including, but not limited to, cardiovascular, peripheral-vascular, cardio-thoracic, gynecological, neuro- and general abdominal surgery.

For example, the adhesive or sealant may be used as an internal surgical adhesive in orthopedic procedures such as anterior cruciate ligament repair, meniscal tear repair (or as a hydrogel for the replacement of the meniscus), posterior capsule reconstruction, rotator cuff repair, and as a bone adhesive. It could also be used as an adhesive for lung volume reduction, patch fixation, subcutaneous tissue repair, and aortic dissection. In particular, it can be used as stomach adhesive for stomach volume reduction, and as adhesive for mesh fixation for hernia repair, drain fixation, valve attachment, attachment for adhesion prevention films, attachment of tissue to tissue (e.g. synthetic or biologic tissue scaffold to tissue, bioengineered tissue to tissue), tissue to device (e.g. mesh, clip, film) and device to device.

Second, the adhesive or sealant can be used for subcutaneous tissue repair and for seroma prevention in procedures such as mastectomy, breast reconstruction & augmentation, reconstructive or cosmetic abdominoplasty and liposuction, face lift, C-section, hysterectomy in obese patients, orthopedic on thigh region, incisional hernia repair, lipoma excision, traumatic lesions, fistula treatment, graft fixation, and nerve repair.

Third, the adhesive or sealant can be used as a sealant to attach and seal dural patch products, bile duct, bile leaks in liver bed, bladder leaks, bone graft, burn graft dressing and liquid occlusive dressing. As a sealant, it can be coated on tissue, device, and tissue-device interface and it can be used as dural—cranial sealant, dural—spine sealant, cardio/peripheral vascular sealant, GI sealant (e.g. esophagus, intestine, large organ, pancreas, stomach, and gastric ulcer), lung sealant, soft organ sealant (e.g. liver, spleen, pancreas), bonewax substitute, tumor sealant, staple/glue combination, sealant, hemostats combination, urethra sealant. It can be used in procedures including, but not limited to, gastric bypass, parenchymatous organs resection, tracheostomy, ulcerative colitis diverticulosis, radical prostatectomy, sinus reconstruction, sternotomy, choledochoduodenostomy, and gallbladder bed sealing, and cholecystectomy. Additionally, the adhesive or sealant may be coated on medical devices such as sutures or staples.

Fourth, the adhesive or sealant can be used as a filler or a periurethral bulking agent in procedures including, but not limited to, dead space removal in reconstructive and cosmetic surgeries, (e.g. plastic/cosmetic/reconstructive, face/facial defect, or void filling), urinary incontinence and other gynecologic procedures, anal fissure/fistula, catheter injection into myocardium for treating congestive heart failure, nuclear augmentation, pancreatic/hepatic cyst/fistula obliteration, and pediatric esophogeal fistula.

Fifth, the adhesive or sealant can be used as a matrix for tissue engineering (e.g. tissue scaffolds, delivery matrix for cells, delivery matrix for brachytherapy (radiation therapy) agents, delivery matrix for growth factors, injection matrix for in situ-forming empty cell scaffold, injection matrix for scaffold for delivery of stem cells, cell lysate, or other biologics, bioactives, pharmaceuticals, and neutraceuticals, localization matrix for chemotherapy, and localization matrix for contrast agent.

Sixth, the adhesive or sealant can be used as an adhesion prevention barrier in procedures such as cardiac, open chest, general surgery, obstetrics and gynecological surgeries, orthopedic surgeries, and spine (e.g. artificial disk).

Seventh, the adhesive or sealant can be used as an occluding material for embolization (e.g. GI Fistula, cerebral/vascular occlusive brain aneurism, tubal occlusion, and varicose vein occlusion).

The Derivatized Tertiary Amine Intermediate

Described herein are derivatized tertiary amine intermediates of tetrakis(2-hydroxypropyl) ethylenediamine (referred to herein as TKHPED), available under the tradename Quadrol from BASF and an analogous compound tetrakis(2-hydroxyethyl) ethylene diamine (referred to herein as TKHEED, available from TCI America, Inc.), generally represented by the following formula of a tertiary diamine core.

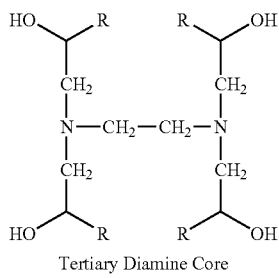

Tertiary Diamine Core where $R=CH_3$(TKHPED), H(TKHEED), $CH_3CH_2$ or other alkyl groups.

A derivatized tertiary amine may be generally represented by Formula I.

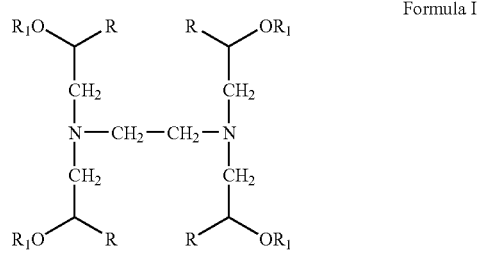

Formula I where $R=CH_3$, H, $CH_3CH_2$ or other alkyl group; and $R_1=H$, $C(O)CH_2OCH_2COOH$, $C(O)(CH_2)_nCOOH$ with n=1-4, or combinations thereof.

Alternatively, the derivatized tertiary amine may be represented by Formula Ia when each of $R_1$ of Formula I has a carboxylic end group

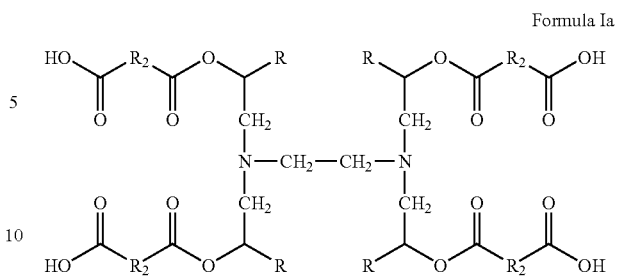

Formula Ia where $R=CH_3$, H, $CH_3CH_2$ or other alkyl groups; and $R_2=CH_2OCH_2$ or $(CH_2)_n$ with n=1-4.

As an example, the carboxyl derivatized tertiary amine of Formula I, having hydrolytically degradable ester linkages, may be synthesized, for example, by reacting tetra(2-hydroxypropyl) ethylenediamine with an anhydride such as glutaric anhydride, succinic anhydride or diglycolic anhydride, in the presence of catalytic amounts of a base, such as triethylamine. The reaction may be carried out in the presence of other bases such as pyridine, or even without a base since the tertiary nitrogen of tetra(2-hydroxypropyl) ethylenediamine may self-catalyze the reaction.

Alternatively, the derivatization of the tertiary diamine core may be partial, producing none, one, two or three carboxylic end groups. An example of a partially derivatized tertiary amine having three carboxylic end groups is shown in Formula I'.

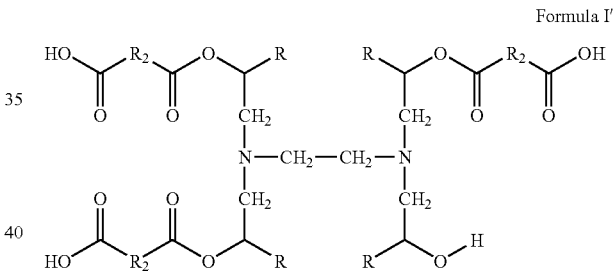

Formula I' where $R=CH_3$, H, $CH_3CH_2$ or other alkyl groups; and $R_2=CH_2OCH_2$ or $(CH_2)_n$ with n=1-4.

The Electrophilic Moiety of Derivatized Tertiary Amine Monomer

The derivatized tertiary amine represented by Formula I may be further converted to a derivatized tertiary amine monomer having electrophilic functional end groups generally represented by Formula II, where the electrophilic functional end group or moiety may be derived from an isocyanate, N-hydroxysuccinimide, N-hydroxymaleimide, or aldehyde.

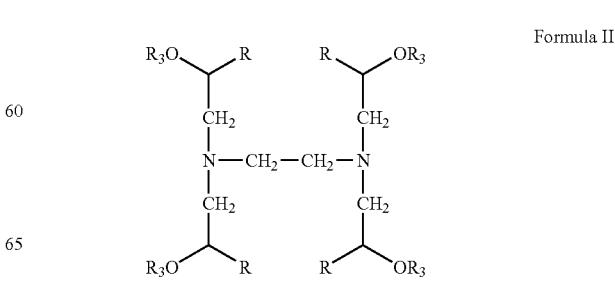

Formula II where R=CH₃, H, CH₃CH₂ or other alkyl groups; and R₃=C(O)OX, C(O)CH₂OCH₂Y, C(O)(CH₂)ₙY or combinations thereof, where X=NHS or NHM, n=1-4 and Y=NCO, C(O)O(NHS), C(O)O(NHM) or C(O)H. As used herein, NHS refers to the radical of N-hydroxysuccinimide, represented by (CH₂)₂(CO)₂N— or

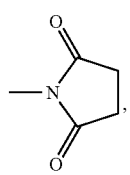

and NHM refers to the radical of N-hydroxymaleimide, represented by (CH₂)₂(CO)₂N—.

Alternatively, a derivatized tertiary amine monomer derived from the derivatized tertiary amine of Formula Ia may be represented by Formula IIa.

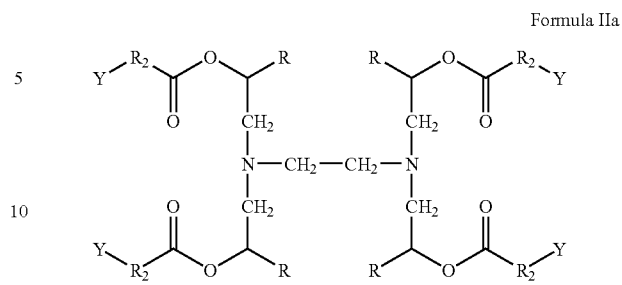

Formula IIa where R=CH₃, H, CH₃CH₂ or other alkyl group; R₂=CH₂OCH₂ or (CH₂), where n=1-4, Y=NCO, C(O)O (NHS), C(O)O(NHM) or C(O)H. As used herein, NCO refers to the radical of isocyanate.

Specific examples of Formula II are represented by Formula A (Q-Glu-NHS), Formula B (Q-Digly-NHS), Formula C (T-Glu-NHS) and Formula D (T-Digly-NHS).

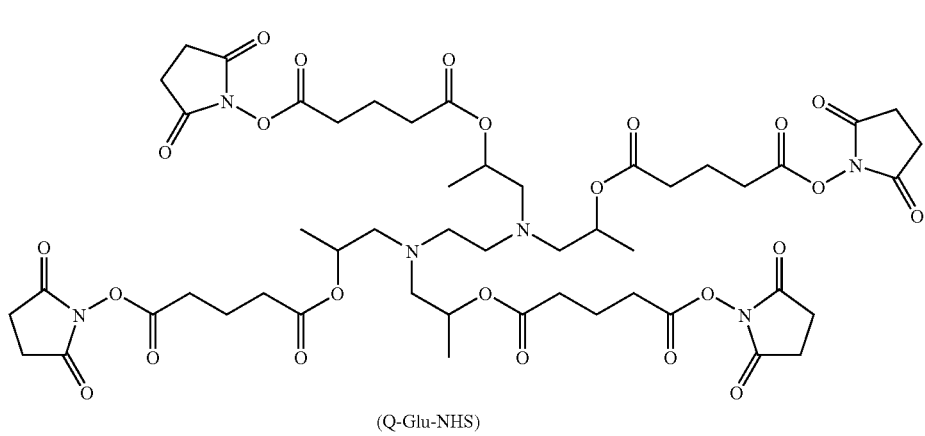

Formula A (Q-Glu-NHS)

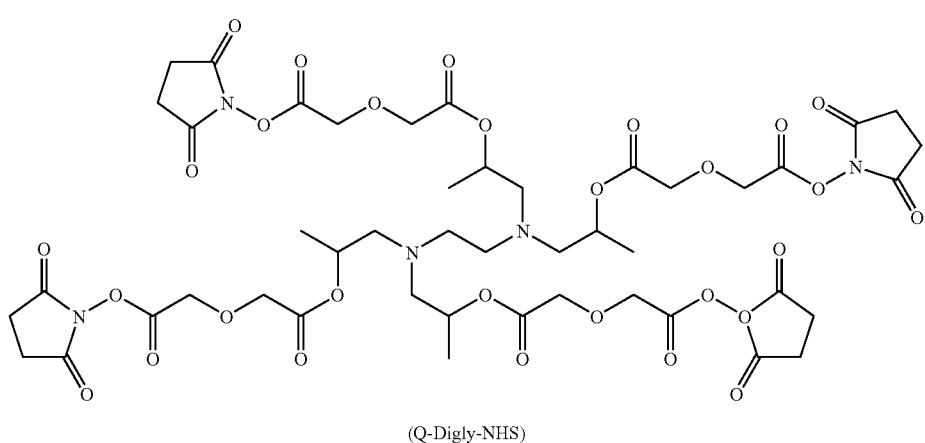

Formula B (Q-Digly-NHS)

-continued

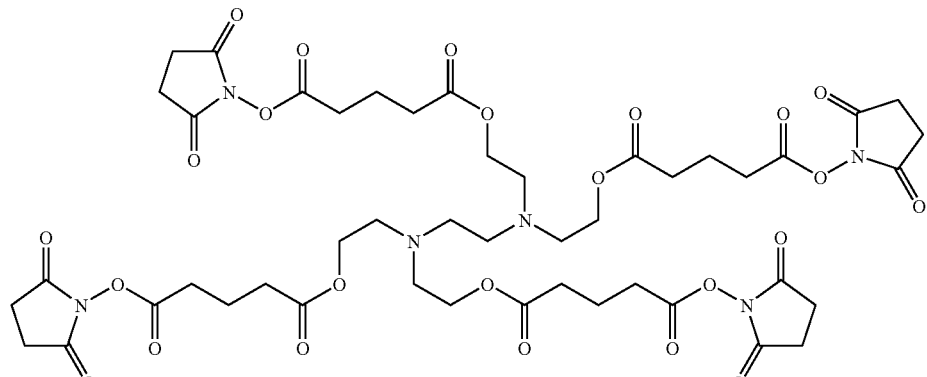

(T-Glu-NHS)

Formula C

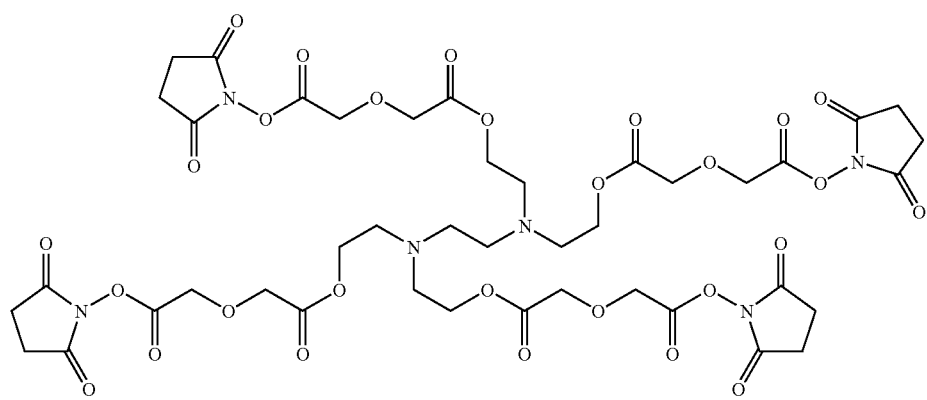

(T-Digly-NHS)

Formula D

It is also possible to have partial derivatization of the carboxyl derivatized tertiary amine of Formula I to yield a partially derivatized monomer with an electrophilic functionality of 1, 2, or 3, as shown in Formula IIa'. For example, it is possible to have either partial or full deriviatization when the electrophilic functional end group is derived from N-hydroxysuccinimide, N-hydroxymaleimide, or an aldehyde. However, it is only possible to have full deriviatization when the electrophilic functional end group is derived from an isocyanate.

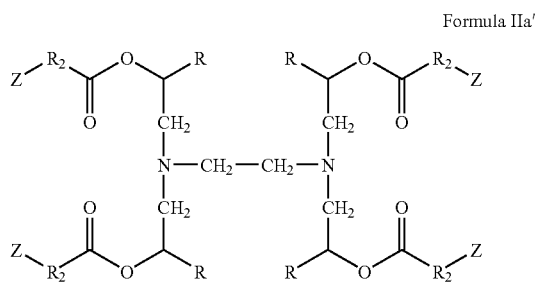

Formula IIa' where R=$CH_3$, H, $CH_3CH_2$ or other alkyl groups; $R_2$=$CH_2OCH_2$, $(CH_2)_n$ with n=1-4, and Z=COOH, C(O)O(NHS), C(O)O(NHM), C(O)H or combinations thereof.

The partially derivatized tertiary amine having three or less carboxylic end groups of Formula I' may also be derivatized with electrophiles to produce derivatized tertiary amine monomers, for example, as shown by Formula II'.

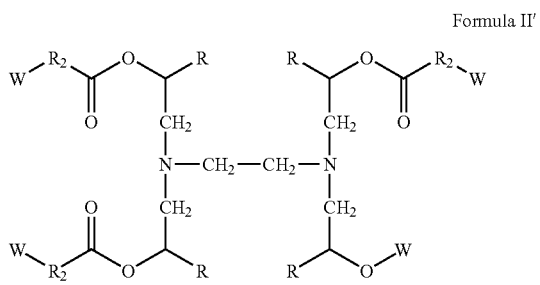

Formula II' where R=$CH_3$, H, $CH_3CH_2$ or other alkyl group; and $R_2$=$CH_2OCH_2$, $(CH_2)_n$ with n=1-4, and W=C(O)O(NHS) or C(O)O(NHM).

Alternatively, the derivatized tertiary amine monomer having electrophilic functional end groups may be represented by Formula III, when the electrophilic end groups are NHS or NHM. In yet another alternative, the monomer may includes ester and carbonate linkages, where the number of carbonate linkages may be one, two, three or four, depending on the number of carboxylic end groups in Formula I.

Formula III

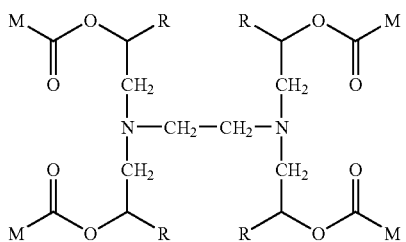

where R=CH$_3$, H, CH$_3$CH$_2$ or other alkyl groups; and M=O (NHS) or O(NHM).

An example where the hydroxyl groups of the tertiary amine core are capped with NHS to form carbonate linkages is shown below in Formula E (Q-Carbonate-NHS)

Formula E

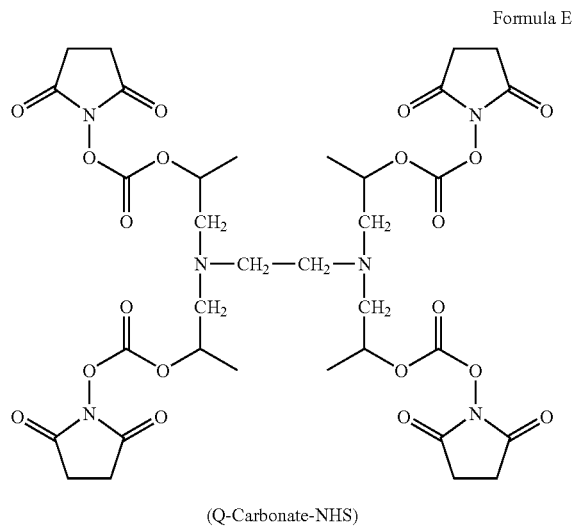

(Q-Carbonate-NHS)

The NHS derivatized tertiary amine monomer may be made by coupling an N-hydroxysuccinimide (NHS) group to the carboxyl derivatized tertiary amine by reaction with disuccinimidyl carbonate (DSC) in the presence of catalyst such as triethylamine or pyridine, or alternatively by condensation of the tertiary diamine core (e.g. TKHPED, TKHEED) with propanoic acid, 3-[(2,5-dioxo-1-pyrrolidinyl)oxy]-3-oxo (or functional equivalent moieties with other alkyl or alkoxy groups). Derivatized tertiary amine monomers having electrophiles derived from N-hydroxylmaleimide or N-hydroxylglutaramide may be made in a similar fashion.

The carboxyl derivatized tertiary amine may be converted into an isocyanate-containing monomer via Curtius rearrangement. Specifically, the carboxyl derivatized tertiary amine may be first converted into an acyl chloride by reacting it with thionyl chloride, which may then be reacted with azidotrimethylsilane to obtain the acyl azide. The acyl azide is then slowly heated to about 65° C. to convert the acyl azide into the isocyanate derivatized tertiary amine monomer.

An aldehyde derivatized tertiary amine monomer may be made by reacting the carboxyl derivatized tertiary amine in the presence of dehydrating agent, such as dicyclohexyl carbodiimide. Alternatively, the electrohilic moieties may be attached to the starting diamines, TKHPED or TKHEED, by derivatizing the hydroxyl group. For example, the aldehyde derivatized tertiary amine monomer may be obtained by reacting TKHPED with glutaraldehydic acid (or related compounds in the series with different number of alkyl groups) in the presence of a dehydrating agent such as a carbodiimide.

The Resultant Adhesive or Sealant

The electrophilic moieties described herein are reactive molecules that may be reacted with any nucleophilic moiety, having an amine or thiol functionality, to form an adhesive, sealant or resultant polymer composition. Several combinations of the electrophilic monomers described herein and various nucleophilic moieties have been shown to react and form a crosslinked polymer that adheres to tissue. The resultant polymer may be in various forms, such as a compliant gel or as a coating.

The nucleophilic moiety, preferably one with an amine functionality, may be derived from a biological source or synthetically modified polysaccharides, where amine groups can be obtained via deacetylation. Examples of biological sources of the nucleophilic moiety include, but are not limited to proteins such as albumin, and epsilon-polylysine, polysaccharides such as chitosan, hyaluronic acid and glycosaminoglycans. Additionally, activated polysaccharides such as amine functionalized carboxymethylcellulose (CMC), synthetic polymers such as amine or thiol functionalized polyethylene glycol (PEG), or polylysine may be used as the nucleophilic moiety. Other suitable nucleophilic moieties include but are not limited to poly(ethylene oxide)imine.

The electrophilic moiety described herein may be reacted with a nucleophilic moiety in a equivalent weight ratio. Equivalent weight as used herein refers to molar weight divided by total number of electrophilic or nucleophilic functionalities. The range of equivalent weight ratio can be from about 1:10 to 10:1.

When the electrophilic functional end group is NHS, polymerization with a nucleophilic amine moiety occurs via formation of an amide linkage, and the generation of N-hydroxysuccinimide (an N-Hydroxy compound of small molecule) as the condensation by-product, as generally represented by Reaction Scheme I.

Reaction Scheme I

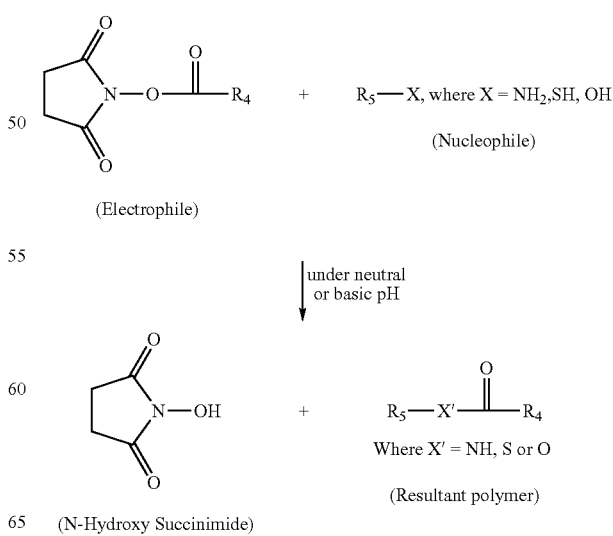

where $R_4$ may be the residue of the derivatized tertiary amine, for example, of Formula Ia, where the carboxyl group may be condensed with N-hydroxysuccinimide, and $R_5$ may be the residue of an amine or thiol containing moiety.

If it is desirable to use an adhesive or sealant in liquid form, the components of such an adhesive or sealant should be water soluble or at least soluble in a water-miscible organic solvent such as acetone, alcohol or a carbonate such as propylene carbonate. For example, the electrophilic monomers represented by Formula A (Q-Glu-NHS) and Formula C (T-Glu-NHS) are viscous liquids at ambient temperature, and are about 60% (wt/wt) soluble in propylene carbonate as observed in 3 to 5 minutes at ambient temperature. The diglycolate monomers represented by Formula B (Q-Digly-NHS) and Formula D (T-Digly-NHS), although powdery solids at ambient temperature, are about 60% (wt/wt) soluble in propylene carbonate. Preferably, the solvent for the electrophilic moiety is propylene carbonate. Suitable solvents for the nucleophilic moieties include, but are not limited to propylene carbonate and N-methylpyrrolidone.

If it is desirable to use an adhesive or sealant in liquid form, the components of such an adhesive or sealant should be reasonably stable in the water or water-miscible solvent at least during the time of application. Depending on the stability thereof, the electrophilic monomers described herein may be stored with or without a solvent prior to use. For example, in the case where storage is desired, the solvent is preferably a water-miscible organic solvent such as propylene carbonate. Where the stability of the electrophilic monomer in the solvent is reasonably good, the solvent and electrophilic monomer may be admixed and stored. If the stability of the electrophilic monomer in the solvent is poor and/or storage is undesirable, the solvent and electrophilic monomer may be admixed just minutes prior to application to the desired site, and then further admixed with a nucleophilic moiety that is either in solvent-free form or in the same solvent as the electrophile. The electrophilic moiety may also be directly mixed with the nucleophilic moiety in water or water-miscible solvent. For example, the diglycolate monomer represented by Formula D is highly soluble in an aqueous solution, but not very stable therein. In this case, it may be desirable to admix the monomer just minutes before delivery to the desired site, with a nucleophilic moiety such as albumin that is already admixed or stored in an aqueous solution.

Preferred electrophilic monomers for use in an aqueous solution form are the monomers represented by Formulae C and D, while preferred nucleophiles are albumin and epsilon-polylysine. For example, (1) the monomer represented by Formula D with albumin may be used at equivalent weight ratio close to 1:1; (2) the monomer represented by Formula D with epsilon-polylysine may be used at equivalent weight ratio of 1:2; (3) the monomer represented by Formula C with albumin may be used at equivalent weight ratio close to 1:1; and (4) the monomer represented by Formula C with epsilon-polylysine may be used at equivalent weight ratio of 1:2

It may be desirable to use the adhesive or sealant components in powder or solid form, with or without a substrate. For example, the monomer represented by Formula D is highly soluble in an aqueous solution and may be used in powder form. The nucleophilic moiety in the case where the adhesive or sealant components are in powder or solid form is preferably albumin, epsilon-polylysine or PEG-amine. The cure time of these moieties ranges from about 1 to 3 minutes based on visual observation of formation of a compliant gel. Further, the adhesive or sealant components may be used in a powder or solid form in combination with a knitted, woven or nonwoven matrix or substrate of oxidized regenerated cellulose (ORC), glycolide-lactide copolymers or a combination thereof. Suitable substrates for use with the adhesive or sealant components may be absorbable or nonabsorbable.

Preferred electrophilic monomers for use in powder or solid form, with or without a substrate, are the monomers represented by Formulae B and D, while preferred nucleophiles are 4-arm PEG amines and epsilon-polylysine. For example, (1) the monomer represented by Formula D with a 4-Arm-PEG Amine may be used at equivalent weight ratio close to 1:1; (2) the monomer represented by Formula D with epsilon-polylysine may be used at equivalent weight ratio of 1:4; (3) the monomer represented by Formula B with 4-Arm PEG-Amine may be used at equivalent weight ratio close to 1:1; and (4) the monomer represented by Formula B with epsilon-polylysine may be used at equivalent weight ratio of 1:4.

Alternatively, if it is desirable to use the adhesive or sealant components in paste form, the electrophilic moiety and a water soluble nucleophilic moietiy may be stored in or admixed prior to use with a water-miscible solvent in which only the electrophilic moiety is soluble. Upon contact with water, preferably physiological fluid that is present at the site of application, the nucleophilic moiety becomes solubilized and is capable of reacting with the electrophilic moiety to form an adhesive or sealant at the site of application.

The resultant polymer composition may be also function as a coating that is applied to any medical device, including but not limited, sutures, staples, vascular grafts, suture knot clip, orthopedic pins, clamps, screws, and plates, clips (e.g., for vena cava). For example, the medical device may be coated with a solution of the nucleophilic moiety followed by a coating with a solution of the electrophilic moiety, and the nucleophilic and electrophilic moieties are allowed to react to form a crosslinked polymer that functions as a coating on the device. In the case of a suture or staple, it may be desirable to have a coating that swells upon contact with physiological fluid after the suture or staple is used to close a wound, thereby sealing the hole that is formed from a suture needle or the staple. Therefore, it may be preferable to utilize PEG amines as the nucleophilic moiety, since PEG based materials are known to swell upon contact with water.

Degradation Products

As discussed above, the adhesive or sealant that is formed in situ should biodegrade over time into degradation products that are water soluble, so that the degradation products can be eliminated naturally either by secretion or incorporation into the natural biochemical cycle.

As shown in Reaction Scheme I where the electrophilic functional end group is NHS, the polymerization with the nucleophilic moiety occurs via formation of an amide linkage, and the generation of an NHS alcohol, which is water-soluble and would be excreted from the body.

Once the resultant adhesive or sealant is formed in situ, the polymer may degrade over time via hydrolysis or enzymatic degradation. For example, degradation of the ester linkages in the resultant polymer may generate the tertiary diamine core, e.g. TKHPED or TKHEED, and the nucleophile coupled to a diacid moiety with an amide link. Where a urethane linkage is formed from the reaction of a nucleophilic moiety and an electrophile having a carbonate NHS, the degradation of the urethane linkage will generate the nucleophilic moiety and the tertiary diamine core. The cleavage of the ester linkage via hydrolysis is expected to occur over a period ranging from about 1 day to 6 days, while the degradation of the urethane linkages is expected to take up to six months. If the nucleophilic moiety is albumin, for example, the degradation of the resulting polymer is via both enzymatic and hydrolytic degradations. The enzymatic degradation of the albumin containing fragment is expected to range from about 1 day to 6 months. If the nucleophilic moiety is epsilon-polylysine or a PEG-amine, for example, the degradation of the resulting polymer is hydrolytic, and the degradation of the epsilon-polylysine or PEG-amine fragment is expected to range from about 1 day to 6 months. All resulting degradation products are water soluble and would be excreted from the body.

Example 1

Synthesis of Carboxyl Derivatized Tertiary Amine Intermediate of Formula I

Formula I with R=$CH_3$ and $R_1$=$(CH_2)_3$ was synthesized as follows.

To 6.97 g of tetra(2-hydroxypropyl) ethylenediamine in 75 mL of dry ethylacetate is added 11.3 g of glutaric anhydride under inert atmosphere. The mixture is stirred under nitrogen overnight. To the clear liquid is added 100 mL of ethylacetate and washed with 2×50 mL of water. The organic layer is dried over anhydrous sodium sulfate. Volatiles were removed to obtain 16.89 g of viscous liquid.

Example 2A

Synthesis of Electrophilic Monomer of Formula A

TKHPED (50 g, 171 mmol) was dissolved in 500 ml dry acetonitrile and glutaric anhydride (79 g, 692 mmol) was added. There was a slight exotherm and the solution was then stirred at ambient temperature for 3 hours. Disuccinimidyl carbonate (185 g, 722 mmol) and pyridine (60 ml) were added and the reaction stirred at ambient temperature overnight. The reaction evolved gas and the disuccinimidyl carbonate slowly dissolved. The solvents were removed under reduced pressure and the residue was dissolved in 1 liter of ethyl acetate. The solution was washed three times with 500 ml water. The organic phase was dried over magnesium sulfate and the solvent removed under reduced pressure to give 160 g of a sticky solid. After solvent removal, the product was a viscous liquid.

Example 2B

Synthesis of the Electrophilic Monomer of Formula B

TKHPED (40 g, 137 mmol) was dissolved in 150 ml DMF and diglycolic anhydride (64 g, 552 mmol) was added. There was a slight exotherm and the solution was then stirred at ambient temperature for 3 hours. Disuccinimidyl carbonate (148 g, 578 mmol) and pyridine (48 ml) were added and the reaction stirred at ambient temperature overnight. The reaction evolved gas and the disuccinimidyl carbonate slowly dissolved. The solvents were removed under reduced pressure at 60° C. and the residue was dissolved in 1 liter ethyl acetate. The solution was washed three times with 250 ml water. The organic phase was dried over magnesium sulfate and the solvent removed under reduced pressure to give 88.5 g of foam. The foam was pulverized to a powder with a mortar and pestle and bottled. Upon heating it softens and turns to liquid over a wide range of temperature between 45-65° C.

Example 2C

Synthesis of the Electrophilic Monomer of Formula C

TKHEED (40 g) and ethoxyquin (1 g) were dissolved in dry acetonitrile (400 mL) and pyridine (60 mL). The solution was purged with argon and glutaric anhydride (80 g) added. A slight exotherm was observed just after addition of the anhydride. The solution was then stirred at ambient temperature for 3 hours. Disuccinimidyl carbonate (185 g) was added and the reaction stirred at ambient temperature overnight. The reaction evolved gas and the disuccinimidyl carbonate slowly dissolved. When a homogeneous solution was observed, the solvents were removed under reduced pressure and the residue was dissolved in acetonitrile (1 L) and the solution diluted with dichloromethane (1 L). The resulting solution was washed two times with brine (500 mL each time). The organic phase was dried over magnesium sulfate and the solvent removed under reduced pressure. The residue was dissolved in acetonitrile (200 mL) and ethyl acetate (2 L) slowly added. The resulting mixture was allowed to settle for at least 1 hour and the liquor decanted. The procedure was repeated twice and the solvent from the combined liquor was removed under reduced pressure to give a sticky, viscous liquid (45 g).

Example 2D

Synthesis of the Electrophilic Monomer of Formula D

TKHEED (50 g, 212 mmol) and ethoxyquin (2 g) was suspended in 300 ml dry acetonitrile and 150 ml pyridine with an argon purge. Diglycolic anhydride (100 g, 862 mmol) was added. There was a slight exotherm and the mixture became homogeneous. The solution was then stirred at ambient temperature for 3 hours. Disuccinimidyl carbonate (225 g, 877 mmol) was added and the reaction stirred at ambient temperature overnight. The reaction evolved gas and the disuccinimidyl carbonate slowly dissolved. The solvents were removed under reduced pressure and the residue (400 g) was dissolved in 200 ml dry acetonitrile. Two 75 mL portions of the solution were placed in 2×250 ml centrifuge bottles and 175 ml of isopropyl alcohol was added to each bottle. The mixture was stirred and then centrifuged. The liquor was decanted and the residue from each bottle was taken up in 25 ml of dry acetonitrile. The procedure was repeated twice more. After three treatments with isopropyl alcohol, the residue in each bottle was dissolved in 25 ml dry acetonitrile and 175 ml of 60:40 ethyl acetate/hexane was added. The mixture was stirred and then centrifuged. The liquor was decanted and the procedure was repeated. The residue in each bottle was dissolved in dry acetonitrile and both solutions were transferred to a 3 L flask. The product (50 g) was dried to an off-white foam under reduced pressure. The remainder of the material was processed in a similar manner to give 180 g of product. The foam was crushed to a powder and transferred to a bottle. Upon heating it softens and turns to liquid over a wide range of temperature between 40-55° C.

Example 2E

Synthesis of the Electrophilic Monomer of Formula E

TKHPED (40 g, 137 mmol) was dissolved in 250 ml of dry acetonitrile in a 2 L flask with a mechanical stirrer. Disuccinimidyl carbonate (211 g, 824 mmol) and triethylamine (157 ml) were added and the mixture was stirred at ambient temperature overnight. The resulting slurry was filtered and the collected solids were washed with acetonitrile. The organic layer was concentrated at reduced pressure and the resultant residue was dissolved in 800 ml of methylene chloride. The methylene chloride solution was washed with 500 ml of 5% citric acid solution, 500 ml water, and then 500 ml of saturated sodium bicarbonate solution in a successive manner to yield an organic phase and aqueous phase The organic phase was dried over magnesium sulfate and the solvent removed under reduced pressure to give 88 g of the electrophilic monomer of Formula E in the form of a foam. The resulting foam was pulverized to a powder with a mortar and pestle and bottled.

Example 3A

A Dry Preparation and its Acute Efficacy in Hemostasis on a Spleen or Liver Model The monomer represented by Formula D and a tetra-arm Polyethylene Glycol-Amine (PEG-Amine) of molecular weight 4,000 were dry blended at a ratio close to the stoichiometric 1:1 in their equivalent weights. Four squares of 1"×1" were cut from a large piece of substrate comprised of a nonwoven polyglactin substrate needle punched with a knitted oxidized regenerated cellulose material, and used as a carrier of the powder. Approximately 0.25 g of the monomer was mixed with 0.89 g of the PEG-Amine in a vial, and then about 4 g of HFE 7000 solvent was added to the mixture. This mixture was vortexed so that the two solids were evenly distributed in the volatile liquid. The resulting slurry was poured onto the nonwoven substrate. The ratio of dry powder to nonwoven substrate was maintained at 70 to 30 by weight. The HFE 7000 was allowed to evaporate for 5 minutes under ambient conditions and the resulting dry patch was then stored under inert atmosphere until use.

The dry patch was applied on the bleeding site of an incision on a porcine spleen with the powder facing the tissue. A wet gauze was applied with mild pressure on top of the patch for one to three minutes, with increments of ½ minute per observation, and visually verified for hemostasis. Hemostasis was observed in two to three minutes. The cured crosslinked polymer bonded to the underlying wet tissue and acted as a sealant to stop bleeding. The same methodology was repeated with a circular incision of a coin-size lesion with a biopsy punch on a porcine liver. Hemostasis again was accomplished in two to three minutes.

Example 3B

Efficacy of a Sealant Patch on Porcine GI Tissue using an Ex Vivo Model as Measured by Burst Pressure The patch described above in Example 3A was used for measuring wet adhesion and burst test. The test set up included a GI section from porcine intestine mounted on a fixture, where the two open ends were connected by tubing to a pressure gauge and a syringe air pump in series. A 1 cm incision was made on the GI section with a single suture closure at the center of the incision. The patch with powder was placed over the 1 cm incision (with the suture at center) on the GI section, and then a wet gauze was applied over the patch until the resulting polymer was cured. After 3 minutes, when curing was complete, the patch bonded to the GI tissue covering the defect. The GI section with the patch was submerged in DI water and the syringe air pump was started to inflate the GI section. Observation of bubbles from the bonded construction marked the failure point and the pressure was recorded as the "burst pressure" in mm of mercury.

The base line burst pressure without any defect in porcine GI tissue was about 100 mm Hg. The observed burst pressure for a defect of 1 cm incision with a single loop suture without the use of the patch was only 1-2 mm Hg. When the patch was applied over the sutured incision, observed burst pressures were in the range of 10 to 90 mm Hg. A typical burst pressure of 25 mm Hg or higher was typically considered an acceptable level of bonding between sealant and tissue.

Burst pressures were also recorded using several patches made from the monomer represented by Formula D with different nucleophiles, at ratio of 70 to 30 by weight for dry powder to matrix. The observed burst pressures were 41 mm Hg with albumin; 68 mm Hg with PEG-amine; and 41 mm Hg with epsilon-polylysine.

Example 3C

An Aqueous Solution Based Two-component Sealant for Bonding to a Tissue 0.63 g of 40 wt/wt % albumin in phosphate buffered saline solution was drawn into a 1 mL Norm-JECT syringe and set aside. In a separate 1 mL Norm-JECT syringe, the plunger was removed and 0.11 g of pulverized monomer represented by Formula D powder was added to the barrel. The plunger was replaced and the monomer containing syringe was attached to the albumin containing syringe via a female-to-female Luer adapter. The syringes were expressed back and forth about 20 times (in 30 seconds) to mix the materials. The syringe containing the mixed components was now in one barrel and the contents were expressed onto freshly harvested porcine intestine or pericardium. A strip of polypropylene mesh was laid on top of the mixed components and left undisturbed to cure for an additional 6 minutes. The T-peel was measured using an Instron, where the resultant polymer and mesh was peeled from the underlying tissue at an angle of 90° at a constant rate of pull of 20 cm per minute Specifically, the measured T-peel on porcine pericardium was 0.58+/−0.06 N/cm (N=4; mode of failure=cohesive) for a resultant polymer prepared from a non-sterile mixture of the monomer represented by Formula D dissolved directly into a 40% solution of albumin in PBS to give a total % solids of 48% (equivalent weight ratio of Formula D to albumin was 1:1); and 0.70+/−0.15 N/cm (N=5; mode of failure=cohesive) for sterile samples of the mixture irradiated at 25 kGy. The data for porcine intenstine T-peel were 0.51+/−0.03 N/cm (N=5, mode of failure=cohesive) and 0.52+/−0.05 N/cm (N=5 mode of failure=cohesive) for non-sterile and sterile, respectively.

The measured T-peel on porcine pericardium was 0.79+/−0.07 N/cm (N=5; mode of failure=mixed of cohesive and adhesive) for a resultant polymer prepared from a mixture of the monomer represented by Formula C in a 40% solution was mixed with the 40% albumin solution in PBS at pH 7.3 at a % solids of 40% (equivalent weight ratio of Formula D to albumin was 1.3:1); and its porcine intestine T-Peel was 0.58+/−0.03 N/cm (N=5; mode of failure=mixed of cohesive and adhesive).

The measured T-peel on porcine pericardium was 0.52+/−0.01 N/cm (N=5; mode of failure=mixed of cohesive) for a resultant polymer prepared from sterile mixture of the monomer represented by Formula C in a 40% solution mixed with the 40% epsilon-polylysine solution in hydrochloric acid where its pH was adjusted to 7.3 and which had a % solids of 40% (equivalent weight ratio of Formula C to epsilon-polylysine was 1:2.4); and its porcine Intestine T-Peel was 0.50+/−0.02 N/cm (N=5; mode of failure=mixed of cohesive and adhesive).

Example 3D

A Paste Based Two-component Sealant for Bonding to a Tissue

A 40% (wt/wt) solution of the monomer of Formula B in polypropylene carbonate was blended with a dry powder of bovine albumin at a solids ratio of Formula B to albumin of about 30 to 70 (wt/wt) to form a paste. The paste was then applied over a 1 cm incision made on the GI section of porcine intestine with a single suture closure at the center of the incision. A wet gauze was applied over the site for 3 minutes, and the burst test was conducted underwater. The burst pressure was determined to be 37 mm Hg (range of 29 to 58 mm Hg).

Example 3E

A Swellable Coating for Sutures and Staples for Leak Prevention or Reduction

Two different crosslinked polymers were prepared using four-arm-PEG-amine of molecular weight 4 k as the nucleophilic moiety and the monomer represented by (i) Formula A (Q-Glu-NHS) and (ii) Formula E (Q-Carbonate-NHS). Specifically, a 20% solution by weight of the electrophilic monomer was prepared in 1-Methyl-2-Pyrrolidone (NMP), and a 30% solution by weight of PEG-amine was also prepared in NMP.

Polypropylene monofilament suture of size 5-0 was treated in a plasma chamber to improve its wetting characteristics for coating. The suture was then dipped in the PEG-amine solution followed by drying in an air-driven oven at 80° C. for about 20 minutes. Thereafter the suture was dipped in electrophilic solution (i) and dried again at 80° C. for about 20 minutes to form a layer of crosslinked polymer. The process was repeated in a sequential manner to obtain five layers of crosslinked polymer, and a final outermost layer of the PEG-amine nucleophilic moiety. The resultant coating was approximately 10% of the diameter of the uncoated suture. Swelling of the coating was observed under the optical microscope in a minute or two upon contact with water. The diameter after swelling was observed to be about 100% of the diameter of the uncoated sutures.

The coated suture using electrophilic solution (i) was run through an ePTFE graft tubing that was connected in series to a pressure gauge and a syringe pump filled with saline, under dry conditions. Thereafter the graft was filled with saline by slowly inflating the pressure in the graft with the syringe pump. The leak pressure through the suture hole was determined. The coated suture showed a higher pressure at the point where a leak was observed compared to an uncoated suture.

Titanium staples used with linear and circular staplers were coated using the electrophile solution (ii) and the same procedure to coat the sutures above. The coated staples were dried by hanging the staples on a suspended suture tied on a stand. Swelling of the coating was observed under a microscope upon contact with water. The coating was present on the staple after firing from a stapler, where it rubbed against the metal anvil in the process of firing.

A 10 cm bowel section of porcine intestine (GI) was pulled through a stapler platform and one side of the GI was stapled. The GI was affixed to a test jig with umbilical tape. The jig was connected to an air pump and a pressure transducer before submerging it under water. The pump was turned on and the leak pressure was recorded as the pressure at the first observation of air leakage under water through the staple hole. The average leak pressure for an uncoated Echelon 60 staple was 43 mm Hg (with N=5, and standard deviation=9 mm Hg), while the coated staple made from the electrophilic solution (ii) and the PEG-amine nucleophilic moiety showed a leak pressure of 72 mm Hg (with N=5 and standard deviation=13 mm Hg).

What is claimed is:

1. An adhesive or sealant system comprising:
   a. one or more derivatized tertiary amine monomer represented by formula

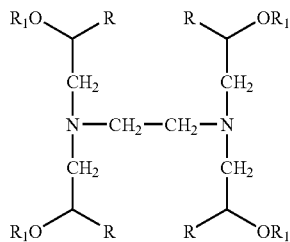

where R=CH$_3$, H, CH$_3$CH$_2$ or other alkyl groups; and R$_3$=C(O)OX, C(O)CH$_2$OCH$_2$Y, C(O)(CH$_2$)$_n$Y or combinations thereof, where X=NHS or NHM, n=1-4 and Y=NCO, C(O)O(NHS), C(O)O(NHM) or C(O)H; and (b) one or more nucleophilic moiety having amine or thiol functionality.

2. The adhesive of claim 1, wherein components (a) and (b) are maintained separately prior to use in a medical application.

3. The adhesive of claim 1, wherein components (a) and (b) are admixed.

4. The adhesive of claim 1, wherein components (a) and (b) are admixed prior to use in a medical application.

5. An adhesive, sealant or polymer that is the reaction product of one or more derivatized tertiary amine monomer represented by formula

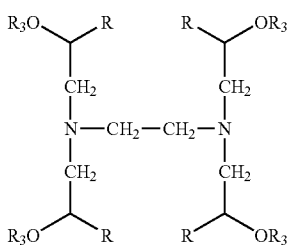

where R=CH$_3$, H, CH$_3$CH$_2$ or other alkyl groups; and R$_3$=C(O)OX, C(O)CH$_2$OCH$_2$Y, C(O)(CH$_2$)$_n$Y or combinations thereof, where X=NHS or NHM, n=1-4 and Y=NCO, C(O)O(NHS), C(O)O(NHM) or C(O)H;

and one or more nucleophilic moiety having amine or thiol functionality.

6. The adhesive or sealant system of claim 1, further comprising an absorbable or nonabsorbable substrate; and (a) a dry blend of i. one or more monomers selected from the group consisting of a

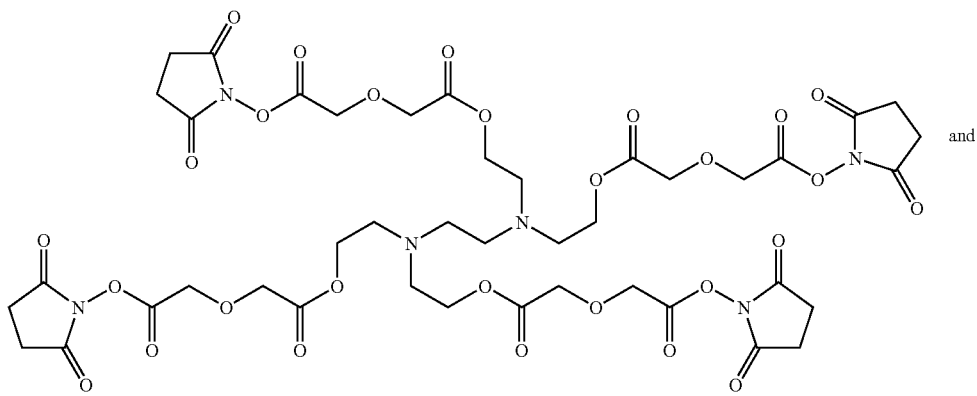

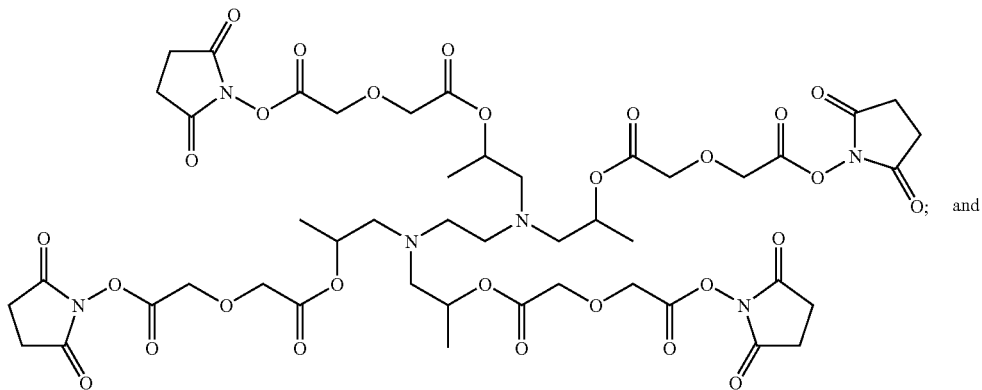

ii. a water soluble nucleophilic moiety having amine functional groups on the substrate.

7. The adhesive or sealant system according to claim 6, wherein the nucleophilic moiety is epsilon-polylysine, polylysine or a PEG-amine.

8. The adhesive or sealant system of claim 1, further comprising a delivery device having at least a first and second chamber; where at least one monomer selected from the following is in the first chamber

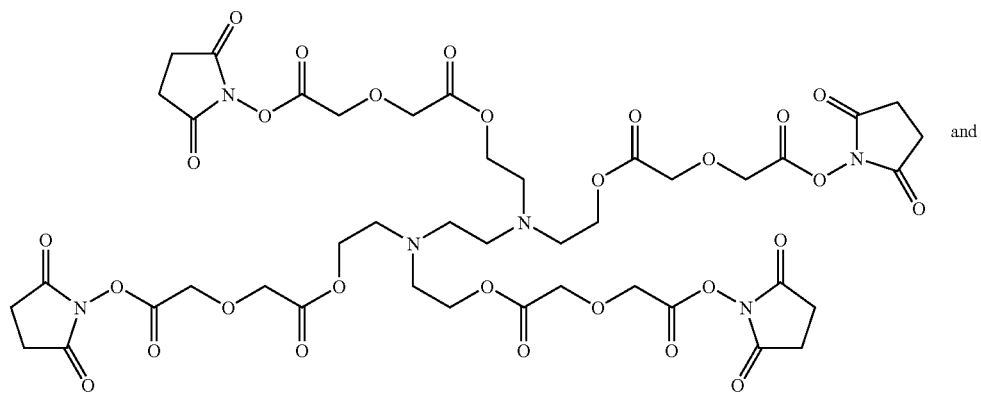

and

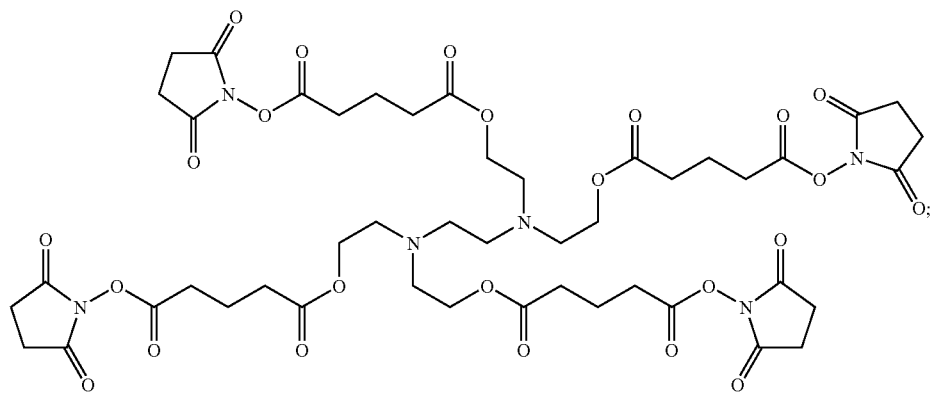

and
a water soluble nucleophilic moiety having amine functional groups is in the second chamber.

9. The adhesive or sealant system according to claim 8, wherein the nucleophilic moiety is albumin or epsilon-polylysine.

10. The adhesive or sealant system according to claim 9, where the nucleophilic moiety is in an aqueous solution in the second chamber.

11. The adhesive or sealant system of claim 1, in the form of a paste and comprising a monomer represented by the following formula

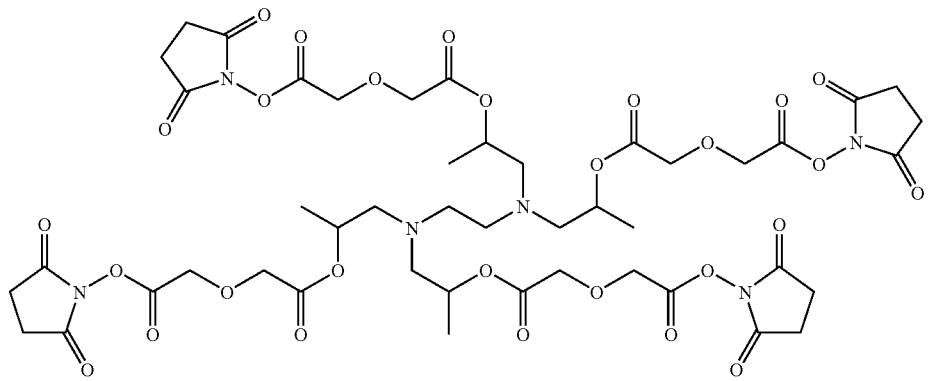

and albumin.

12. A medical device comprising a suture, staple, vascular graft, suture knot clip, orthopedic pin, clamp, screw, plate or clip, and the polymer of claim 5 coated thereon.

13. The medical device of claim 12, where the polymer is the reaction product of

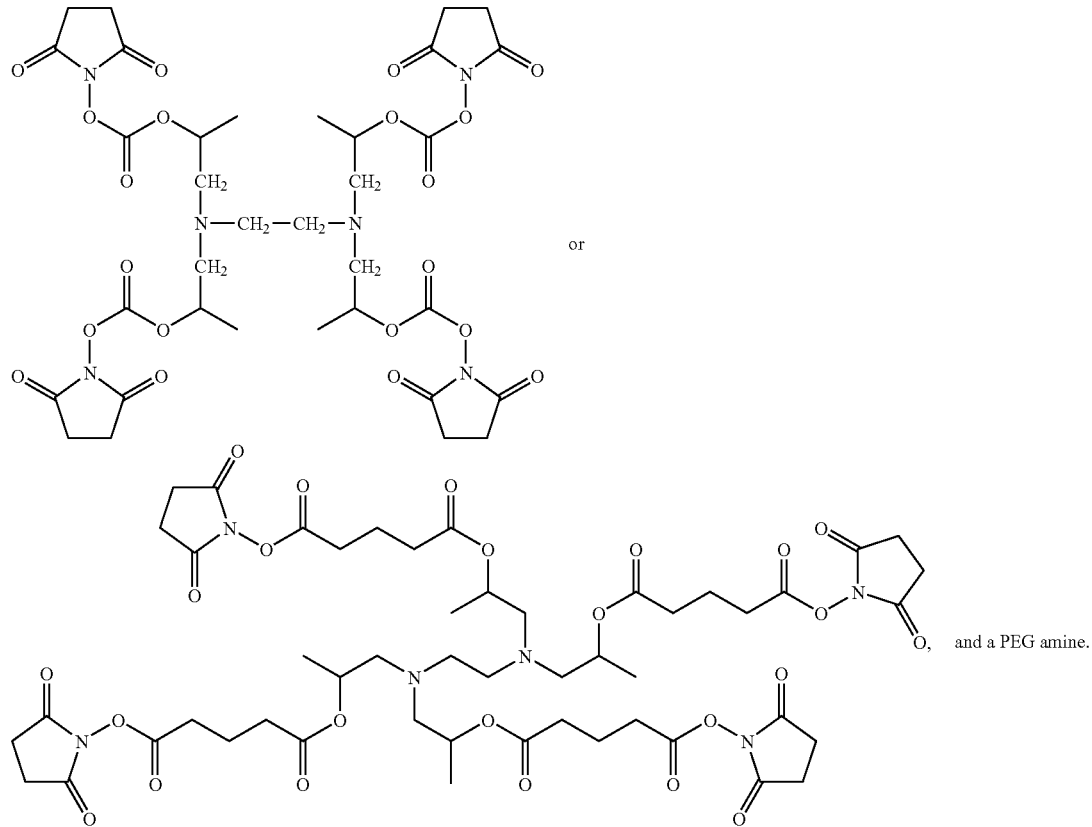

and a PEG amine.

* * * * *

UNITED STATES PATENT AND TRADEMARK OFFICE
CERTIFICATE OF CORRECTION

| | |
|---|---|
| PATENT NO. | : 7,868,123 B2 |
| APPLICATION NO. | : 11/942035 |
| DATED | : January 11, 2011 |
| INVENTOR(S) | : C. A. Khatri et al. |

It is certified that error appears in the above-identified patent and that said Letters Patent is hereby corrected as shown below:

Column 18, line 40, replace each instance of the $R_1$ substituent with an $R_3$ substituent Signed and Sealed this
Twenty-second Day of February, 2011

David J. Kappos
*Director of the United States Patent and Trademark Office*